United States Patent
Ho et al.

(10) Patent No.: US 10,405,785 B2
(45) Date of Patent: Sep. 10, 2019

(54) DETERMINATION OF A CONCENTRATION OF AN ANALYTE IN A SUBJECT

(71) Applicant: City University of Hong Kong, Kowloon (HK)

(72) Inventors: Derek Ho, Diamond Hill (HK); Wenrong Yan, Kowloon (HK); Liping Wei, Kowloon (HK); Yi Tian, Kowloon (HK)

(73) Assignee: CITY UNIVERSITY OF HONG KONG, Kowloon (HK)

( * ) Notice: Subject to any disclaimer, the term of this patent is extended or adjusted under 35 U.S.C. 154(b) by 366 days.

(21) Appl. No.: 15/228,482

(22) Filed: Aug. 4, 2016

(65) Prior Publication Data

US 2018/0035933 A1    Feb. 8, 2018

(51) Int. Cl.
   *A61B 5/1455*    (2006.01)
   *A61B 5/145*     (2006.01)
   *A61B 5/00*      (2006.01)

(52) U.S. Cl.
   CPC ...... *A61B 5/14556* (2013.01); *A61B 5/14532* (2013.01); *A61B 5/6815* (2013.01);
   (Continued)

(58) Field of Classification Search
   CPC . A61B 5/0013; A61B 5/1455; A61B 5/14551; A61B 5/14532; A61B 5/14556;
   (Continued)

(56) References Cited

U.S. PATENT DOCUMENTS

| 2002/0016534 A1* | 2/2002 | Trepagnier ........... A61B 5/0059 600/316 |
| 2004/0073119 A1* | 4/2004 | Mycek ................ A61B 5/0059 600/476 |

(Continued)

OTHER PUBLICATIONS

D. I. Ellis, and R. Goodacre, "Metabolic fingerprinting in disease diagnosis: biomedical applications of infrared and Raman spectroscopy," Analyst, vol. 131, No. 8, pp. 875-885, 2006.

(Continued)

*Primary Examiner* — Eric F Winakur
*Assistant Examiner* — Chu Chuan Liu
(74) *Attorney, Agent, or Firm* — Renner Kenner Greive Bobak Taylor & Weber

(57) ABSTRACT

A method for determining a concentration of an analyte in a subject includes irradiating a part of the subject with electromagnetic radiation, wherein a part of the subject comprises biological molecules arranged to absorb the electromagnetic radiation and to emit fluorescence in response. The method also includes measuring fluorescence emitted to obtain data representative of a fluorescence decay. The method further includes processing the data to determine one or more feature points associated with the fluorescence decay and to generate one or more feature vectors based on the one or more feature points, and applying the one or more feature vectors to a regression model for the analyte to determine the concentration of the analyte. Also provided is a system for determining a concentration of an analyte in a subject, as well as a measurement device for facilitating determination of a concentration of an analyte in a subject.

52 Claims, 8 Drawing Sheets

(52) U.S. Cl.
CPC .......... *A61B 5/6826* (2013.01); *A61B 5/7203* (2013.01); *A61B 5/7225* (2013.01); *A61B 5/7267* (2013.01); *A61B 5/7278* (2013.01); *A61B 2562/0238* (2013.01)

(58) Field of Classification Search
CPC ... A61B 5/6815; A61B 5/6826; A61B 5/7203; A61B 5/7225; A61B 5/7278; A61B 5/7267
See application file for complete search history.

(56) References Cited

U.S. PATENT DOCUMENTS

| | | | |
|---|---|---|---|
| 2007/0156036 A1* | 7/2007 | Pilon | A61B 5/0059 600/310 |
| 2007/0197880 A1* | 8/2007 | Maynard | A61B 5/0071 600/300 |
| 2009/0101843 A1* | 4/2009 | Henshaw | G01J 3/28 250/484.4 |
| 2011/0077473 A1* | 3/2011 | Lisogurski | A61B 5/14551 600/301 |
| 2013/0135580 A1* | 5/2013 | Hartung | A61B 3/0008 351/204 |
| 2016/0354039 A1* | 12/2016 | Soto | A61B 5/7275 |

OTHER PUBLICATIONS

R. A. Gabbay, and S. Sivarajah, "Optical coherence tomography-based continuous noninvasive glucose monitoring in patients with diabetes," Diabetes technology & therapeutics, vol. 10, No. 3, pp. 188-193, 2008.

S. K. Vashist, "Non-invasive glucose monitoring technology in diabetes management: A review," Analytica chimica acta, vol. 750, pp. 16-27, 2012.

V. M. Monnier, O. Bautista, D. Kenny, D. R. Sell, J. Fogarty, W. Dahms, P. A. Cleary, J. Lachin and S. Genuth, "Skin collagen glycation, glycoxidation, and crosslinking are lower in subjects with long-term intensive versus conventional therapy of type 1 diabetes: relevance of glycated collagen products versus HbA1c as markers of diabetic complications. DCCT Skin Collagen Ancillary Study Group. Diabetes Control and Complications Trial," Diabetes, vol. 48, No. 4, pp. 870-880, 1999.

S.-j. Yeh, O. S. Khaiil, C. F. Hanna, and S. Kantor, "Near-infrared thermo-optical response of the localized reflectance of intact diabetic and non-diabetic human skin," Journal of biomedical optics, vol. 8, No. 3, pp. 534-544, 2003.

P. Oomen, G. Kant, R. Dullaart, W. Reitsma, and A. Smit, "Acute hyperglycemia and hyperinsulinemia enhance vasodilatation in Type 1 diabetes mellitus without increasing capillary permeability and inducing endothelial dysfunction," Microvascular research, vol. 63, No. 1, pp. 1-9, 2002.

R. Badugu, J. R. Lakowicz, and C. D. Geddes, "A glucose-sensing contact lens: from bench top to patient", Current opinion in biotechnology, vol. 16, No. 1, pp. 100-107, 2005.

O. S. Khalil, "Non-invasive glucose measurement technologies: An update from 1999 to the dawn of the new millennium", Diabetes Technology & Therapeutics, vol. 6, No. 5, pp. 660-697, 2004.

A. von Ketteler, D. Siegberg, D. Herten, C. Horn, and W. Petrich, "Fluorescence lifetime-base glucose sensor using NADH", pp. 82290P-82290P-8.

K. M. Katika, and L. Pilon, "Feasibility analysis of an epidermal glucose sensor based on time resolved fluorescence," Applied optics, vol. 46, No. 16, pp. 3359-3368, 2007.

K. M. Katika, and L. Pilon, "Numerical feasibility analysis of an epidermal glucose sensor based on time-resolved fluorescence", pp. 60840Z-60840Z-11.

J. D. Newman, and A. P. Turner, "Home blood glucose biosensors: a commercial perspective," Biosensors and Bioelectronics, vol. 20, No. 12, pp. 2435-2453, 2005.

\* cited by examiner

DETERMINATION OF A CONCENTRATION OF AN ANALYTE IN A SUBJECT

TECHNICAL FIELD

The present invention relates to a method for determining a concentration of an analyte in a subject, a system for implementing the same, and a measurement device in the system. Particularly, although not exclusively, the present invention relates to in vivo noninvasive glucose concentration measurement based on NADH fluorescence decay.

BACKGROUND

The measurement of blood glucose concentration is important for the prevention and control of many chronic and potentially fatal medical conditions such as cardiovascular diseases and diabetes. In order to measure blood glucose level, a user has to use a glucose concentration measurement system. These systems can broadly be classified into two types—invasive type and non-invasive type.

Many of the traditional glucose concentration measurement systems are invasive systems. To measure glucose concentration, a user has to prick the skin (e.g., on a fingertip) to draw a small sample of blood. The blood is transferred to a test strip, which is then inserted into to the system. The system analyzes the blood sample on the test strip to determine the blood glucose level. A reading of the glucose level is displayed to the user on a display means (e.g., screen) of the system. These invasive systems are generally not user-friendly, bulky, and expensive.

Because of the above problems, non-invasive glucose concentration measurement systems have been heavily researched and developed in the last few decades. These non-invasive systems measure glucose level indirectly based on different physical principles, without requiring the creation of a wound to obtain blood sample. Examples of these systems include polarimetry-based systems, impedance-based systems, electrochemistry-based systems, microwave-technique-based systems, and optical-based systems.

In spite of these recent advancements, significant challenges remain for the development of glucose concentration measurement systems. These challenges include: weak detection signal due to relatively low concentration of glucose in blood; detection is susceptible to influence by background tissues (e.g., skin, muscle, etc.); blood volume change caused by cardiac impulse may lead to instability for light intensity based spectrum analysis; optical-based detection devices are generally bulky and expensive. Thus, there remains a need for the development of a more reliable, efficient, and accurate means and method for measuring blood glucose concentration.

SUMMARY OF THE INVENTION

In accordance with a first aspect of the present invention, there is provided a method for determining a concentration of an analyte in a subject, comprising the steps of: irradiating a part of the subject with electromagnetic radiation, wherein the part of the subject comprising biological molecules arranged to absorb the electromagnetic radiation and to emit fluorescence in response; measuring fluorescence emitted from the part of the subject to obtain data representative of a fluorescence decay; processing the data to determine one or more feature points associated with the fluorescence decay and to generate one or more feature vectors based on the one or more feature points; and applying the one or more feature vectors to a regression model for the analyte to determine the concentration of the analyte. The fluorescence from the part of the subject is preferably entirely contributed by the biological molecules. However, in some embodiments, the fluorescence from the part of the subject is only partly contributed by the biological molecules. The regression model for the analyte is preferably trainable by a machine learning model or algorithm using the data or the one or more feature vectors.

In one embodiment of the first aspect, the step of irradiating a part of the subject with electromagnetic radiation comprises the step of transmitting electromagnetic radiation in the form of pulses to the part of the subject. The radiation pulses are preferably of high frequency, for example, up to 1 MHz.

In one embodiment of the first aspect, the step of measuring fluorescence emitted from the part of the subject comprises the steps of detecting fluorescence photons emitted from the part of the subject; and counting a number of fluorescence photons detected.

In one embodiment of the first aspect, the step of measuring fluorescence emitted from the part of the subject further comprises the step of determining, for each detected fluorescence photon, a response time based on a time difference between irradiation of electromagnetic radiation from which the respective fluorescence photon originates and detection of the respective fluorescence photon.

Preferably, the data represents a relationship between the number of fluorescence photons and the response time. Preferably, the data represents a relationship between the number of fluorescence photons, a response time (in some cases referred to as the lifetime) of fluorescence molecules from which the fluorescence photons are emitted, and the chemical composition or process in which the fluorescence molecules reside. The data may comprise a plurality of data points, and they may be presented in the form of a histogram.

In one embodiment of the first aspect, the step of processing the data to determine one or more feature points associated with the fluorescence decay comprises the steps of: filtering the data to reduce noise in the data; and applying a feature point identification method to the filtered data to identify one or more feature points from the data. The filtering may be performed using one or more of a highpass filter, a lowpass filter, a band-pass filter, and a band-stop filter.

In one embodiment of the first aspect, the one or more features points comprise one or more peaks of the fluorescence decay, and so the feature point identification method is a peak identification method.

In one embodiment of the first aspect, the peak identification method comprises the steps of: normalizing the data by dividing the data with a maximum value of the data; calculating a Shannon power using an equation $E=-x^2 \log(x^2)$, where E is the Shannon power and x is the normalized data; normalizing the averaged Shannon power; and applying a threshold to the normalized averaged Shannon power to identify the one or more peaks.

In one embodiment of the first aspect, the step of processing the data to generate one or more feature vectors based on the one or more feature points comprises the steps of: selecting a data subset from the filtered data based on the one or more feature points; processing the data subset; and generating the one or more feature vectors based on the processed data subset.

In one embodiment of the first aspect, the step of processing the data subset comprises the steps of normalizing the data subset, and removing baseline of the data subset.

In one embodiment of the first aspect, the step of generating the one or more feature vectors based on the processed data subset comprises the step of generating the one or more feature vectors using the processed data subset and one or more characteristics associated with the subject.

In one embodiment of the first aspect, the step of generating one or more feature vectors based on the one or more feature points identified comprises the steps of: selecting a data subset around the one or more peaks of the fluorescence decay; normalizing an intensity and length of the data subset; removing a baseline of the data subset; and generating the one or more feature vectors based on the normalized data subset with baseline removed and one or more characteristics associated with the subject.

In one embodiment of the first aspect, the subject is a human or an animal, and the one or more characteristics associated with the subject comprise at least one of: age, weight, and body mass index of the subject.

In one embodiment of the first aspect, the one or more features points comprise one or more of: a fluorescence lifetime value associated with the fluorescence decay; a slope of the fluorescence decay; and a central value of the fluorescence decay fitted with an exponential function.

In one embodiment of the first aspect, the method further comprises the step of selecting the regression model from a plurality of regression models.

In one embodiment of the first aspect, the selected regression model is one of: a general regression model, a personalized regression model for the subject, and a hybrid regression model combining the general regression model and the personalized regression model.

In one embodiment of the first aspect, the method further comprises the step of creating the regression model.

In one embodiment of the first aspect, the step of creating the regression model comprises the step of: performing the steps of irradiating a part of the subject with electromagnetic radiation, wherein the part of the subject comprising biological molecules arranged to absorb the electromagnetic radiation and to emit fluorescence in response; measuring fluorescence emitted from the part of the subject to obtain data representative of a fluorescence decay; and processing the data to determine one or more feature points associated with the fluorescence decay and to generate one or more feature vectors based on the one or more feature points; and measuring the concentration of the analyte in a subject using another method at substantially the same time. Preferably, this step is repeated for a plurality of times. The step of creating the regression model further comprises the step of correlating one or more features vectors obtained by performing the above steps and concentration of the analyte obtained from the another method so as to create the regression model.

In one embodiment of the first aspect, the method further comprises training the regression model with one or more feature vectors using a machine learning based method. The machine learning based method preferably utilizes a support vector machine model.

In one embodiment of the first aspect, the subject is a human or an animal, the biological molecules comprise a reduced form of nicotinamide adenine dinucleotide (NADH), and the analyte comprises glucose. Preferably, the method in an embodiment of the first aspect is performed in vivo.

In one embodiment of the first aspect, the subject is a human or an animal, and the part of the subject comprises one of the following body parts of the subject: earlap, oral mucosa, tip of tongue, fingertip, forehead, lips, and arm.

In accordance with a second aspect of the present invention, there is provided a system for determining a concentration of an analyte in a subject, comprising: a source of electromagnetic radiation arranged to irradiate a part of the subject, wherein the part of the subject comprising biological molecules arranged to absorb the electromagnetic radiation and to emit fluorescence in response; a measurement unit arranged to measure fluorescence emitted from the part of the subject to obtain data representative of a fluorescence decay; and a processor arranged to process the data to determine one or more feature points associated with the fluorescence decay and to generate one or more feature vectors based on the one or more feature points; and apply the one or more feature vectors to a regression model for the analyte to determine the concentration of the analyte. The fluorescence from the part of the subject is preferably entirely contributed by the biological molecules. However, in some embodiments, the fluorescence from the part of the subject is only partly contributed by the biological molecules. The regression model for the analyte is preferably trainable via a machine learning model or algorithm using the data or the one or more feature vectors.

In one embodiment of the second aspect, the source of electromagnetic radiation is arranged to transmit electromagnetic radiation in the form of pulses to the part of the subject. The radiation pulses are preferably of high frequency, say up to 1 MHz.

In one embodiment of the second aspect, the measurement unit comprises a detector arranged to detect fluorescence photons emitted from the part of the subject and a counter arranged to count a number of fluorescence photons detected.

In one embodiment of the second aspect, the processor or a processing sub-unit in the measurement unit is arranged to determine, for each detected fluorescence photon, a response time based on a time difference between irradiation of an electromagnetic radiation from which the respective fluorescence photon originates and collection of the respective fluorescence photon.

In one embodiment of the second aspect, the data represents a relationship between the number of fluorescence photons and the response time. The data may be presented in the form of a histogram.

In one embodiment of the second aspect, the processor is arranged to filter the data to reduce noise in the data, and to apply a feature point identification method to the filtered data to identify one or more feature points from the data. The filtering may performed using one or more of a highpass filter, a lowpass filter, a band-pass filter, and a band-stop filter.

In one embodiment of the second aspect, the processor is arranged to select a data subset from the filtered data based on the one or more feature points; process the data subset; and generate the one or more feature vectors based on the processed data subset.

In one embodiment of the second aspect, the processor is further arranged to generate the one or more feature vectors using the processed data subset and one or more characteristics associated with the subject.

In one embodiment of the second aspect, the subject is a human or an animal, and the one or more characteristics associated with the subject comprises at least one of: age, weight, and body mass index of the subject.

In one embodiment of the second aspect, the processor is further arranged to select the regression model from a plurality of regression models; wherein the selected regression model is one of: a general regression model, a personalized regression model for the subject, and a hybrid regression model combining the general regression model and the personalized regression model.

In one embodiment of the second aspect, the subject is a human or an animal, the biological molecules comprise a reduced form of nicotinamide adenine dinucleotide (NADH), and the analyte comprises glucose.

In one embodiment of the second aspect, the subject is a human or an animal, and the part of the subject comprises one of the following body parts of the subject: earlap, oral mucosa, tip of tongue, fingertip, forehead, lips, and arm.

In accordance with a third aspect of the present invention, there is provided a measurement device for facilitating determination of a concentration of an analyte in a subject, comprising: a light source arranged to irradiate a part of a subject, wherein the part of the subject comprising biological molecules arranged to absorb the electromagnetic radiation and to emit fluorescence in response; and a detector arranged to detect fluorescence emitted from the part of the subject.

In one embodiment of the third aspect, the light source is a high frequency light source comprising an LED or a laser emitter.

In one embodiment of the third aspect, the light source is arranged to provide pulsed light. The light source is preferably a high frequency light source.

In one embodiment of the third aspect, light emitted by the light source comprises a wavelength of 310 nm to 400 nm.

In one embodiment of the third aspect, the detector is a single photon avalanche diode or a photomultiplier tube arranged to count a number of fluorescence photons.

In one embodiment of the third aspect, the measurement device further comprises at least one of an excitation filter and an emission filter, both are which are arranged to filter light emitted from the light source such that the filtered light is adapted for absorption by the biological molecules. The measurement device further comprises a fibre-optic array or a collimator arranged to concentrate the filtered light.

In one embodiment of the third aspect, the measurement device further comprises at least one of an excitation filter and an emission filter, both are which are arranged to filter fluorescence emitted from the part of the subject such that the filtered light is adapted for detection by the detector. The measurement device further comprises a fibre-optic array or a collimator arranged to concentrate the filtered light.

In one embodiment of the third aspect, the light source and the detector are arranged on the same side with respect to the part of the subject.

In one embodiment of the third aspect, the light source and the detector are arranged on opposite sides with respect to the part of the subject.

In one embodiment of the third aspect, the measurement device further comprises a time to digital converter module operably connected with the detector, the time to digital converter module being arranged to determine, for each fluorescence photon, a response time based on a time difference between irradiation of the light from which the respective fluorescence photon originates and collection of the respective fluorescence photon.

In one embodiment of the third aspect, the measurement device further comprises a processor operably connected with the detector and the time to digital converter module to process data obtained by the detector and the time to digital converter module, the data representing a relationship between the number of fluorescence photons and the response time.

In one embodiment of the third aspect, the measurement device further comprises a communication module operably connected with the processor, the communication module being arranged to transfer the data to a remote information handling system for processing and analysis.

In one embodiment of the third aspect, the communication module is a wireless communication module arranged to communicate with external devices using a wireless communication link. The wireless communication link may be a mobile broadband, Bluetooth, ZigBee, NFC, RFID, or Wi-Fi communication link.

In one embodiment of the third aspect, the measurement device is portable. In one embodiment of the third aspect, the measurement device is wearable by a user.

In one embodiment of the third aspect, the remote information handling system is a portable electronic device. The portable electronic device is an information handling system, and can be in the form of a mobile phone, a computer, a laptop, a notebook computer, a tablet computer, etc.

In one embodiment of the third aspect, the remote information handling system comprises: a communication module arranged to receive the data transferred from the communication module of the measurement device; a processor arranged to process the data to determine one or more feature points associated with the fluorescence decay and to generate one or more feature vectors based on the one or more feature points; and apply the one or more feature vectors to a regression model for the analyte to determine the concentration of the analyte.

In one embodiment of the third aspect, the communication module of the remote information handling system is further arranged to: transfer the data to a database for storage; and obtaining one or more regression model from a database with a plurality of regression models for the analyte.

In one embodiment of the third aspect, the processor of the remote information handling system is further arranged to select a regression model from the one or more regression model.

In one embodiment of the third aspect, the database is formed by a server. The server may be an information handling system.

In one embodiment of the third aspect, the measurement device is an integrated time-correlated single-photon counting (TCSPC) device.

In one embodiment of the third aspect, the subject is a human or an animal, the biological molecules comprise a reduced form of nicotinamide adenine dinucleotide (NADH), and the analyte comprises glucose. The part of the subject may be one of the following body parts of the subject: earlap, oral mucosa, tip of tongue, fingertip, forehead, lips, and arm.

BRIEF DESCRIPTION OF THE DRAWINGS

Embodiments of the present invention will now be described, by way of example, with reference to the accompanying drawings in which.

DETAILED DESCRIPTION OF THE PREFERRED EMBODIMENT

Figure 1:
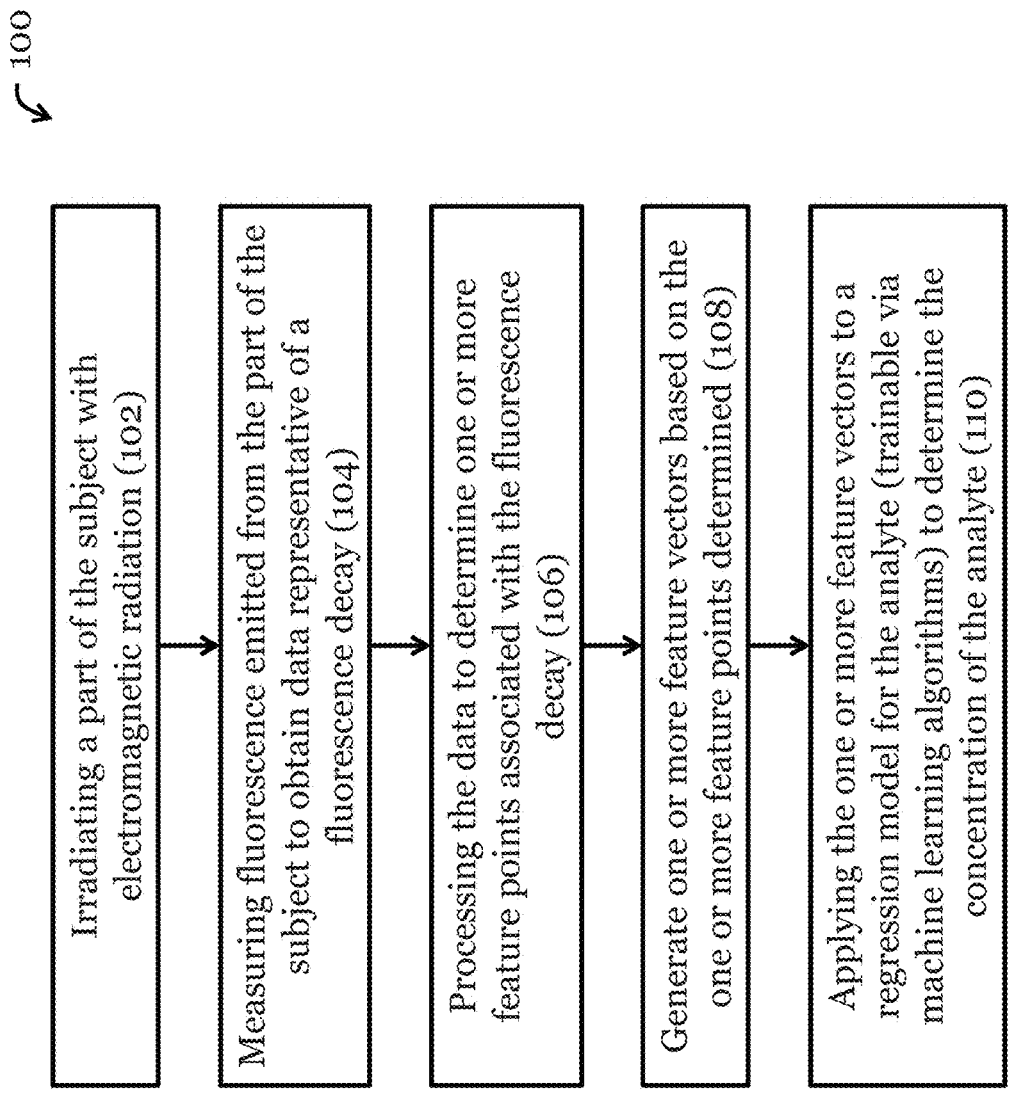
FIG. 1 is a flow diagram showing a method for determining a concentration of an analyte in a subject in accordance with one embodiment of the present invention.

FIG. 1 shows a method for determining a concentration of an analyte in a subject in accordance with one embodiment of the present invention. Preferably, the method is non-invasive and can be performed in vivo and continuously. The subject can be a human or an animal, and the analyte is preferably glucose. The method begins from step 102, in which a part of the subject is irradiated with electromagnetic radiation. The part of the subject includes biological molecules arranged to absorb the electromagnetic radiation and to emit fluorescence in response. The electromagnetic radiation is preferably in the form a pulsed light emitted by, for example, one or more LEDs or laser emitters. In one embodiment, the biological molecules comprise a reduced form of nicotinamide adenine dinucleotide, NADH.

The method further involves, in step 104, measurement of fluorescence emitted from the part of the subject to obtain data representative of a fluorescence decay. Preferably, the fluorescence is substantially entirely emitted by the biological molecules having absorbed the electromagnetic radiation. Such biological molecules may generally be referred to as fluorescence molecules. In another embodiment, the fluorescence may only be partly contributed by the biological molecules. The fluorescence is preferably measured by counting the number of fluorescence photons detected. Preferably, a response time is determined for each detected fluorescence photon, where the response time corresponds to a time difference between irradiation of electromagnetic radiation from which the respective fluorescence photon originates and detection of the respective fluorescence photon. In one embodiment, data representative of the fluorescence decay represents a relationship between the number of fluorescence photons and the response time. In a preferred embodiment, the data represents a relationship between the number of fluorescence photons, a response time (in some cases referred to as the lifetime) of fluorescence molecules from which the fluorescence photons are emitted, and the chemical composition or process in which the fluorescence molecules reside. The data may include a plurality of data points that may be presented in graphical form, e.g., a histogram.

Once the data is obtained, the method proceeds to step 106, in which the data is processed to determine one or more feature points associated with the fluorescence decay. In one embodiment, the data is first filtered to reduce or remove noise in the data. A feature point identification method is then applied to the filtered data to identify one or more feature points from the data. In a preferred embodiment, the one or more features points comprise one or more peaks of the fluorescence decay, and the feature point identification method is a peak identification method. In a preferred embodiment, signal processing is required prior to peak identification so as to remove components from the data that is not associated with the response of the biological molecules. In one embodiment, the one or more features points comprise or further comprise one or more of: a fluorescence lifetime value associated with the fluorescence decay; a slope of the fluorescence decay; and a central value of the fluorescence decay fitted with an exponential function.

In step 108, the data is further processed to generate one or more feature vectors based on the one or more feature points determined. In one embodiment, this may involve selecting a data subset from the filtered data based on the one or more feature points; processing the data subset, for example, by normalizing the data subset, and removing baseline of the data subset; and generating the one or more feature vectors based on the processed data subset. Preferably, the one or more feature vectors are generated using the processed data subset and one or more characteristics associated with the subject. The one or more characteristics associated with the subject may include age, weight, and body mass index of the subject.

In step 110, the one or more feature vectors are applied to a regression model for the analyte to determine a concentration of the analyte. The regression model contains a correlation between the feature vectors and concentration of the analyte. Preferably, the regression model can be trained with data or the one or more feature vectors using machine learning methods such as support vector machine model. The regression model may be a general regression model (e.g., trained with non-specific data/feature vector), a personalized regression model for the subject (e.g., trained with data/feature vector specific to the subject), or a hybrid regression model combining the general regression model and the personalized regression model (e.g., trained with non-specific data/feature vector and data/feature vector specific to the subject).

To further illustrate some embodiments of the present invention, the following description provides a method, a system, and apparatuses for non-invasive and continuous measurement of glucose concentrations based on NADH fluorescence decay. A person skilled in the art would readily appreciate that the method, apparatus, and system described below are not limited in their application for glucose measurement, but can be used in other biological applications for measuring other analyte in the subject.

A method for continuous and non-invasive glucose measurement in one embodiment of the present invention comprises the following steps: (1) acquiring NADH fluorescence decay from the user; (2) identifying the feature point(s) on NADH fluorescence decay; (3) generating feature vector(s) of NADH fluorescence decay; (4) selecting the corresponding glucose regression model of the user from the database of glucose regression; and (5) estimating the user glucose level by importing the feature vector(s) to the glucose regression model. In the embodiment where there is only one regression model in the system, the selection step (4) is not necessary.

In one embodiment, the feature points may be one or more peaks of NADH fluorescence decay. The specific method in step (2) for identifying feature points of NADH fluorescence decay may comprises two steps. The first step involves filtering the data by a low-pass filter to reduce high-frequency noise; and then filtering the data by a high-pass filter to remove baseline fluctuation. The low-pass filter may be a Butterworth low-pass filter, and the high-pass filter may be a Butterworth high-pass filter. Other types of high-pass, low-pass, band-pass, or band-stop filters (for example, Chebyshev filters or Elliptic filters) may be used in some other embodiments. After filtering, the second step involves applying an algorithm to the filtered data to identify or determine one or more feature points of the NADH fluorescence decay. In one embodiment, the algorithm may be one based on Shannon power, which is further explained below. The one or more feature point may include a peak of the NADH fluorescence decay. The peak may not be the peak of the raw data. Preferably, further processing to the data may be required in order to identify the peak.

In one embodiment, the specific method in step (3) for generating one or more feature vectors of NADH fluorescence decay may comprise the following four main steps. The first step involves selection of a subset of data of the NADH fluorescence decay around the one or more peaks of decay identified in step (2). The second step includes normalizing the intensity and length of the subset. The third step includes removing baseline of the subset. In one embodiment, the baseline is defined as a line that passes through the start and the end of the data subset. The fourth and final step involves construction of one or more feature vectors based on the processed data subset. Preferably, the construction of one or more feature vectors also takes into account one or more feature values including age, weight and body mass index of the subject.

In the present embodiment, the glucose regression model can preferably be trained with the one or more feature vectors via a machine learning method. In one embodiment, the glucose regression model may also be trained with the data. The machine learning method is preferably based on statistical learning. In one example, the machine learning method comprises support vector machine (SVM). In one embodiment, the glucose regression model can be created or maintained by performing the following two steps. The first step involves simultaneously acquiring glucose measurements using another invasive or non-invasive method and acquiring glucose measurements based on the above method for obtaining NADH fluorescence decay of NADH from the user. The second step involves training the regression model with one or more feature vector using SVM to obtain, train, and/or optimize the regression model.

Figure 2:
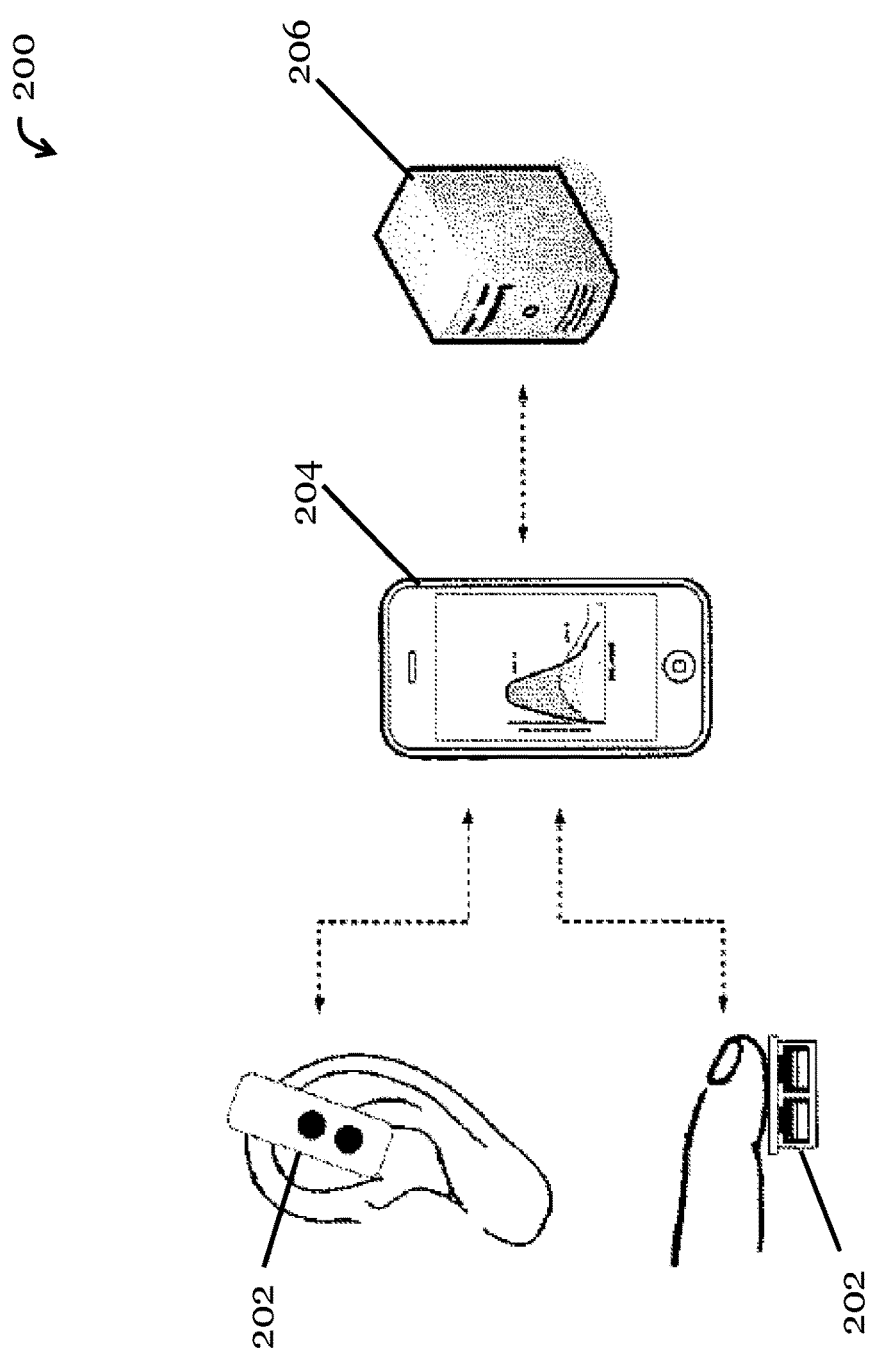
FIG. 2 is an illustration showing a system for implementing the method of FIG. 1 in accordance with one embodiment of the present invention.

FIG. 2 shows a system 200 for implementing the method for determining blood glucose concentration in accordance with one embodiment of the present invention. The system 200 in the present embodiment is a non-invasive continuous NADH fluorescence decay based blood glucose estimation system, and it generally comprises a measurement device 202, an electronic device 204, and a database 206 operably connected through wired or wireless connections. Preferably, the measurement device 202 is portable, and is arranged to be arranged on a body part such as the earlap or the finger tip of the user for measuring blood glucose level. In a preferred embodiment, the measurement device 202 may comprise or is an integrated time-correlated single photon counting (TCSPC) device. The TCSPC device is preferably lens-less. In FIG. 2, the electronic device 204 operably connected with the measurement device 202 is in the form of a mobile phone. In other embodiments, however, the electronic device 204 may be any other information handling systems and can be in the form of, for example, a computer, a laptop, a notebook computer, a tablet computer, etc. The electronic device 204 may in turn be connected with the database 206, which can be in the form of a server or other information handling systems.

In one embodiment, the information handling system that can be used as the electronic device 204 and/or the database 206 may have different forms and configurations. Such information handling system generally comprises suitable components necessary to receive, store, and execute appropriate computer instructions or codes. The main components of such information handling system are a processing unit and a memory unit. The processing unit is a processor such as a CPU, an MCU, etc. The memory unit may include a volatile memory unit (such as RAM), a non-volatile unit (such as ROM, EPROM, EEPROM and flash memory) or both. Preferably, the information handling system further includes one or more input devices such as a keyboard, a mouse, a stylus, a microphone, a tactile input device (e.g., touch sensitive screen) and a video input device (e.g., camera). The information handling system may further include one or more output devices such as one or more displays, speakers, disk drives, and printers. The displays may be a liquid crystal display, a light emitting display or any other suitable display that may or may not be touch sensitive. The information handling system may further include one or more disk drives which may encompass solid state drives, hard disk drives, optical drives, flash drives, and/or magnetic tape drives. A suitable operating system may be installed on the information handling system, e.g., on the disk drive or in the memory unit of the information handling system. The memory unit and the disk drive may be operated by the processing unit. The information handling system also preferably includes a communication module for establishing one or more communication links (not shown) with one or more other computing devices such as a server, personal computers, terminals, wireless or handheld computing devices. The communication module may be a modem, a Network Interface Card (NIC), an integrated network interface, a radio frequency transceiver, an optical port, an infrared port, a USB connection, or other interfaces. The communication links may be wired or wireless for communicating commands, instructions, information and/or data. Preferably, the processing unit, the memory unit, and optionally the input devices, the output devices, the communication module and the disk drives are connected with each other through a bus, a Peripheral Component Interconnect (PCI) such as PCI Express, a Universal Serial Bus (USB), and/or an optical bus structure. In one embodiment, some of these components may be connected through a network such as the Internet or a cloud computing network. A person skilled in the art would appreciate that the information handling system described above is merely exemplary, and that different information handling systems may have different configurations and still be useable as the electronic device 204 and/or the database 206 in the present invention.

Also, although the system 200 in the embodiment of FIG. 2 includes three separate devices, in some embodiments the system may have less than three devices. In one example, the database 206 may be incorporated in the electronic device 204, and as a result the system may not include a separate database 206. In another example, the measurement device 202 and the electronic device 204 may be integrated as a single device. In yet another example, the measurement device 202, the electronic device 204, and the database 206 may be all integrated as a single device.

Figure 3:
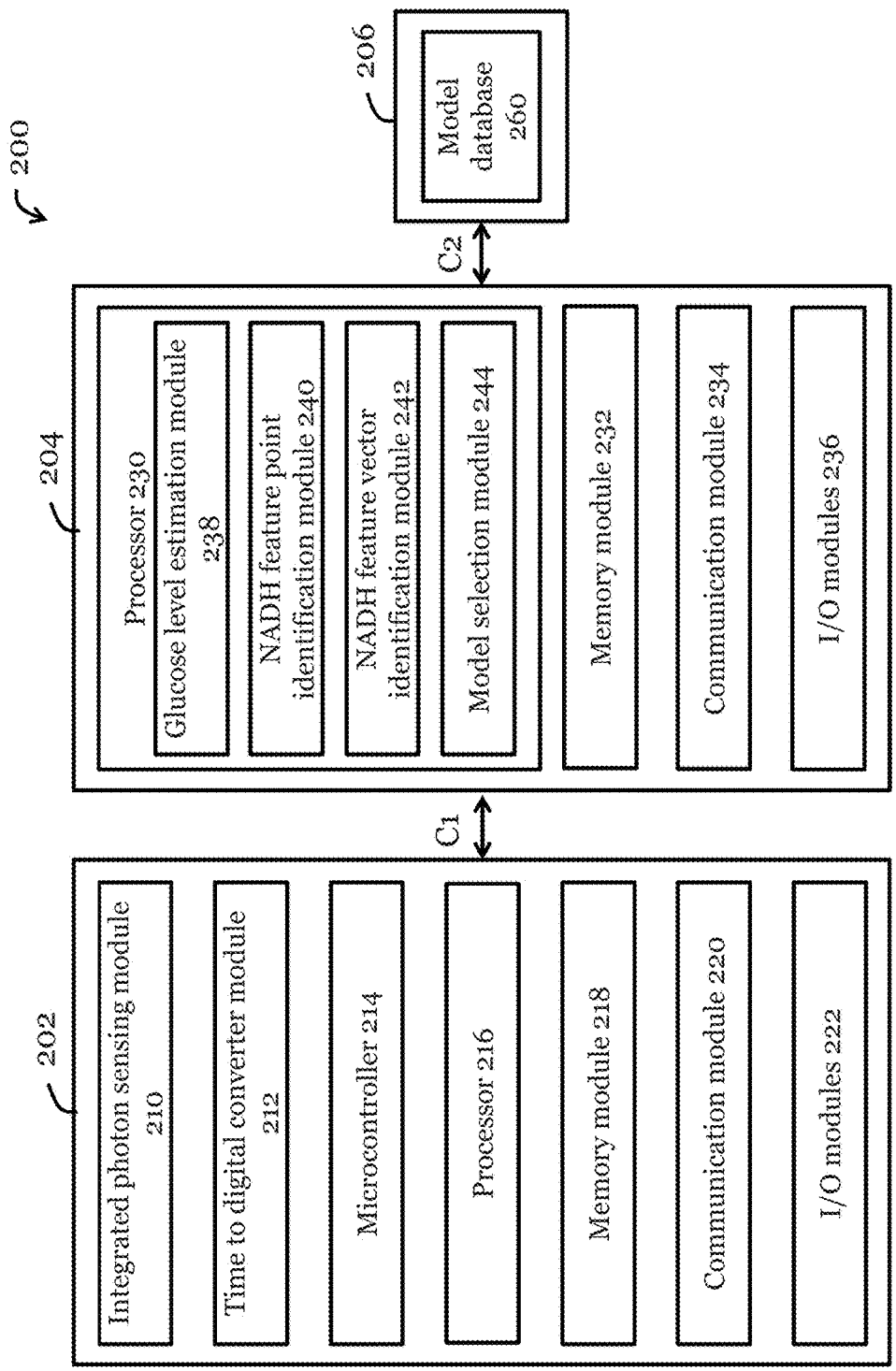
FIG. 3 is a function block diagram of a system for implementing the method of FIG. 1 in accordance with one embodiment of the present invention.

FIG. 3 show a functional block diagram for the measurement device 202, the electronic device 204, and the database 206 in the system 200 of FIG. 2, in accordance with one embodiment of the present invention. A person skilled in the art would appreciate that the functional modules illustrated in FIG. 3 may be implemented by hardware, software, or both. In some embodiments, one or more of the functional modules may be combined. In some embodiments, one or more of the functional modules may be further divided into separate functional modules.

In the embodiment of FIG. 3, the measurement device 202 comprises an integrated photon sensing module 210, a time to digital converter module 212, a microcontroller 214, a processor 216, a memory module 218, a communication module 220, and input/output modules 222 that are operably connected with each other through, for example, one or more data and/or power buses. Preferably, the measurement device 202 also includes a power source (not shown) which may be a battery. The battery may be rechargeable. In some embodiments, the measurement device 202 may be powered by AC power.

Figure 4:
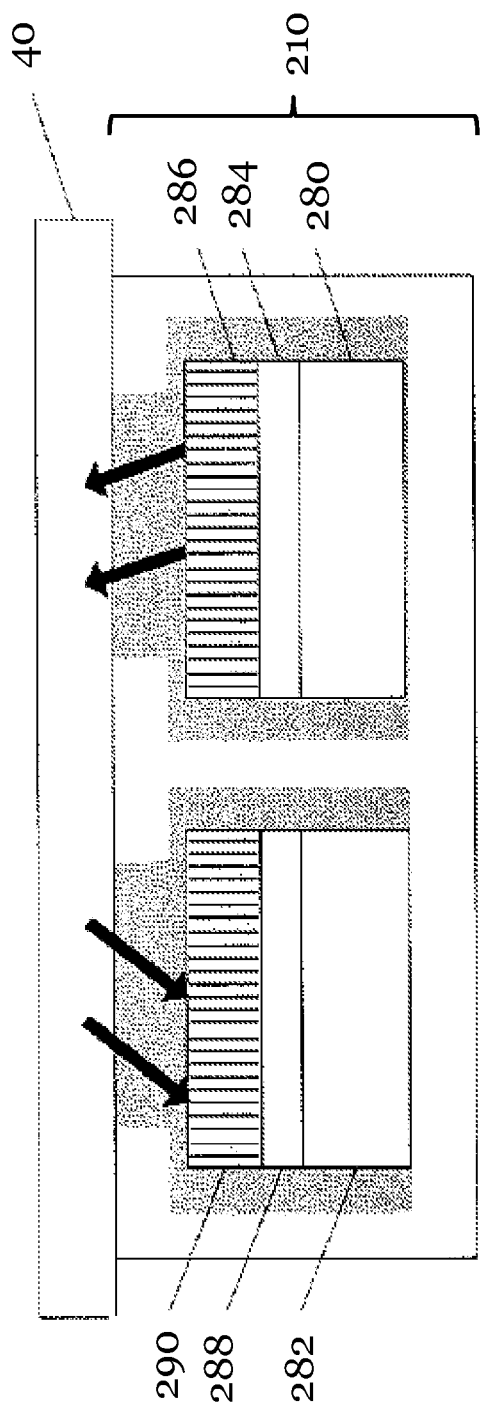
FIG. 4 is a photon sensing module in the measurement device in the system of FIG. 3 in accordance with one embodiment of the present invention.

FIG. 4 shows the basic structure of the integrated photon sensing module 210 in FIG. 3 in accordance with one embodiment of the present invention. As shown in FIG. 4, the module 210 is arranged to be placed close to a target sample 40 for irradiating the target sample and for detecting a response. The target sample 40 may be human or animal body part, such as earlap, oral mucosa, tip of tongue, fingertip, forehead, lips, or arm. In the present embodiment, biological molecules of a reduced form of nicotinamide adenine dinucleotide, NADH, are generally contained in the body part to be irradiated or being irradiated. These NADH molecules are adapted to absorb electromagnetic radiation and to emit fluorescence light in response.

Referring to FIG. 4, the integrated photon sensing module 210 comprises an electromagnetic radiation source 280 arranged to radiate the target sample 40. In one embodiment, the electromagnetic radiation source 280 is a light source formed by one or more light-emitting diodes (LED). Alternatively, the light source may be formed by one or more laser emitters or other radiation emitters. Preferably, the light source is a high frequency pulsed light source arranged to emit pulsed light. In a specific example, the light source may be Nano LED-250 Pulsed LED 250 nm nominal from Horiba Scientific. Preferably, the light source 280 provides energy to be absorbed by NADH, and hence provides energy for NADH fluorescence. In one embodiment, the frequency of the light source pulse can be up to 1 MHz. Preferably, the wavelength of the light from the light source 280 is around UVA waveband (approximately 315-400 nm), the wavelength of which includes the feature absorption peak of NADH.

The integrated photon sensing module 210 further includes a detector 282 arranged to detect the fluorescence light emitted by NADH. In the present embodiment, the detector 282 is a photon counting detector arranged to count the fluorescence photon. Preferably, the detector 282 is a single photon avalanche diode (SPAD) arranged to collect the fluorescence photon emitted from the sample 40. In one particular example, the detector 282 is ID101 detector from ID Quantique SA. The SPAD may have a dead time of up to 35 ns, thus allowing efficient photon collection. Preferably, the SPAD is capable of collecting over ten thousand fluorescence photons every second. In some embodiments, a photomultiplier tube (PMT) may be used in place of the SPAD. In the embodiment shown in FIG. 4, the detector 282 is arranged adjacent to the light source 280, such that the detector 282 and the light source 280 are spaced apart from the target sample 40 by substantially the same distance. Although not shown in FIG. 4, in some embodiments, the detector 282 and the source 280 may be arranged at an angle to each other.

A light source filter 284 may be arranged between the source 280 and the target sample 40. The filter 284 may comprise at least one of an excitation filter and an emission filter. In the present embodiment, the light source filter 284 is used to filter the light source 280 to ensure the wavelength of the light emitted by the source 280 can be concentrated around the feature absorption peak of NADH (enhancing absorption by NADH). In one specific example, the filter 284 may be 49000-ET-DAPI filter from Chroma Technology Corp. Preferably, a light concentrator 286 is arranged between the filter 284 and the target sample 40 for concentrating light to be transmitted to the target sample 4o. The light concentrator 286 may be a fiber-optic array or a collimator. In other embodiments, the light concentrator 286 may alternatively be arranged between the source 280 and the filter 284.

A further filter 288 may be arranged between the target sample 40 and the detector 282. The filter 288 may comprise at least one of an excitation filter and an emission filter. In the present embodiment, the filter 288 is used to filter the light transmitted from the target sample 40 to the detector 282, to ensure that the wavelength of light arrived at the detector 282 is mainly in the frequency range of the fluorescence from NADH. The filter 288 may also help to filter the light based on the frequency response of the detector 282 so as to ensure that the wavelength of light is suitable to be received by the detector 282. In one specific example, the filter 288 may be ET375/10BP filter from Chroma Technology Corp. Preferably, a light concentrator 290 is arranged between the filter 288 and the target sample 40 for concentrating light to be transmitted to the detector 282. The light concentrator 290 may be a fiber-optic array or a collimator. In other embodiments, the light concentrator 290 may be arranged between the detector 282 and the filter 288.

The integrated photon sensing module 210 as shown in FIG. 4 is of a reflective type, wherein the light source 280 and the photon counting detector 282 are arranged on the same side with respect to the target sample. However, in some embodiments, the integrated photon sensing module 210 may be of a transmissive type, wherein the light source 280 and the photon counting detector 282 are arranged substantially opposite each other, separated by the target sample.

Referring back to FIG. 3, the integrated photon sensing module 210 is operably connected with the time to digital converter module 212. In the present embodiment, the time to digital converter module 212 is used to identify the response time (or arrival time) of each received photon by comparing a time difference between signals from the light source 280 (i.e., time of emission of light that generates the respective photon) and the detector 282 (i.e., time of detection of the respective photon). In one example, the time to digital converter module 212 may be TDC7200 time to digital converter chip from Texas Instruments.

The microcontroller 214 in the measurement device 202 is arranged to control and regulate operation of the device 202. The processor 216 is arranged to analyze the collected data to render the statistics of NADH fluorescence decay. In one embodiment, the processor 216 is only arranged to preliminarily process the data obtained, and analysis of the data is performed by a remote information handling system, e.g., electronic device 204. This may reduce the power and performance requirement on the processor and the microcontroller, allowing the measurement device to be made small and portable. Preferably, the microcontroller 214 and the processor 216 are arranged to receive, store, and execute appropriate computer instructions or codes. In the present embodiment, the microcontroller 214 and the processor 216 are provided as separate function modules. However, in practice, they may be provided as a single CPU, MCU, etc. The memory module 218 is arranged to store the raw data and/or the analysed data. As described previously with respect to FIG. 2, the memory module 218 may be a volatile memory unit (such as RAM), a non-volatile unit (such as ROM, EPROM, EEPROM and flash memory), or both.

Figure 6:
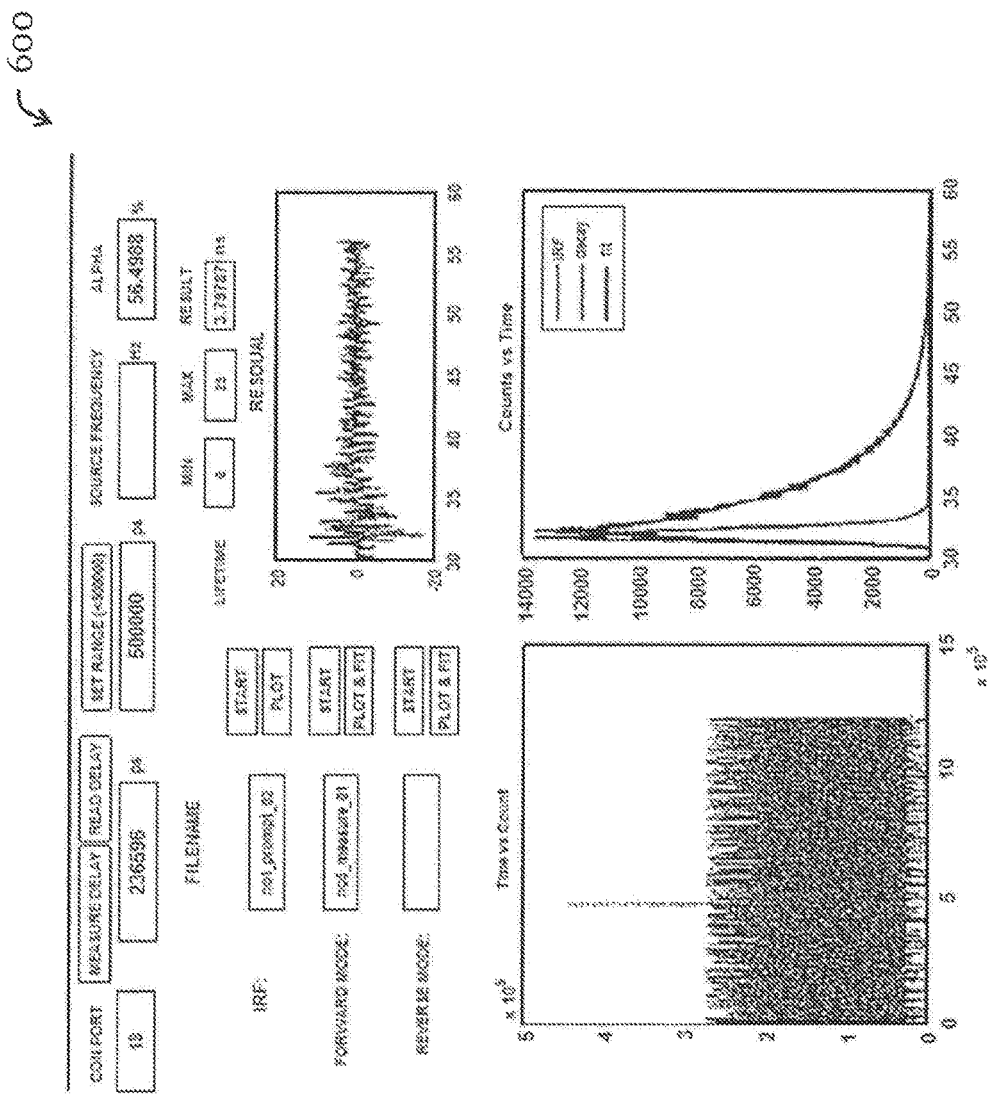
FIG. 6 is a picture showing a graphical user interface of the measurement device of FIG. 3 in accordance with one embodiment of the present invention.

Input/output modules 222 may be provided in the measurement device 202. For example, the input/output modules 222 may include one or more control buttons, a microphone, a touch sensitive input device (e.g., screen), a display, a speaker, etc. In one embodiment, the measurement device 202 includes a display screen and control buttons as the input/output modules 222. Preferably, a graphical user interface is provided by the input/output modules 222 so that the measurement device 202 is arranged to be controlled by a user and to display data, results, or other information to the user. FIG. 6 shows an exemplary graphical user interface 600 of measurement device 202. As shown in FIG. 6, the interface 600 includes photon arrival time and histogram of photon arrival time. The fitting of the decay by the convolution of IRF and NADH fluorescence decay is also shown in the interface 600. A corresponding fluorescence lifetime acquired from the fitting result is also displayed.

The communication module 220 in the measurement device 202 enables data and/or power communication between the measurement device 202 and the electronic device 204 through a communication link C1. Preferably, the communication module 220 allows data to be transferred to the remote electronic device 204 for further processing and analysis. In the present embodiment, the communication module 220 is a wireless communication module arranged to communicate with external devices through a wireless communication link C1. The wireless communication link C1 may be a mobile broadband, Bluetooth, ZigBee, NFC, RFID, or Wi-Fi communication link. In some embodiments, the communication module 220 may be a wired communication module arranged to communication data and/or power with the electronic device 204 through a data and/or power cable.

Figure 5:
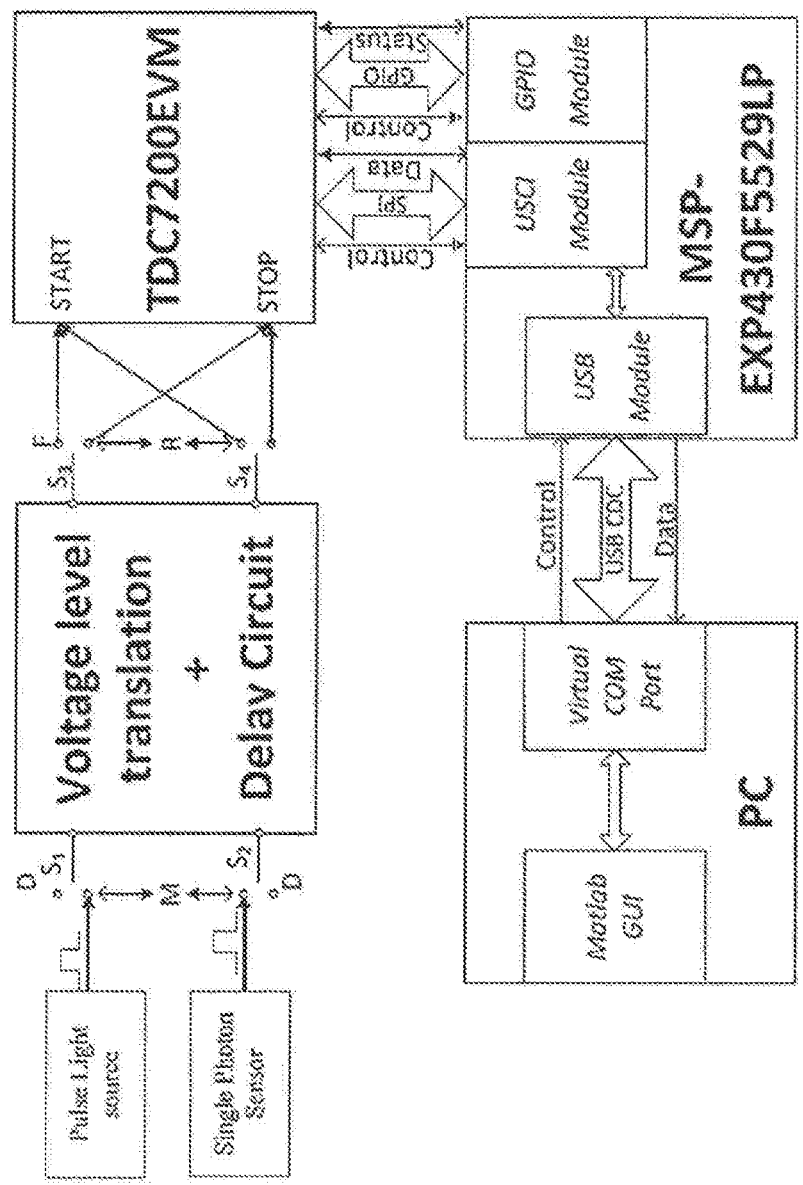
FIG. 5 is a hardware block diagram of the measurement device of FIG. 3 in accordance with one embodiment of the present invention.

FIG. 5 shows a hardware block diagram of the measurement device 202 of FIG. 3 in accordance with one embodiment of the present invention. For accurate measurements, the delay of the transmission cables and circuits in the measurement device 202 needs to be measured a priori. Preferably, the delay information is used for calibration of measured data to improve the accuracy of the measurement.

Referring back to FIG. 3, the electronic device 204 comprises a processor 230, a memory module 232, a communication module 234, and input/output modules 236 that are operably connected with each other through, for example, one or more data and/or power buses. Preferably, the electronic device 204 also includes a power source (not shown) which may be a battery. The battery may be rechargeable. In some embodiments, the measurement device 202 may be powered by AC power. A person skilled in the art would appreciate that the electronic device 204 would have other functional modules for performing other functions that is not directly related to the method of the present invention, and that these other modules are be specifically illustrated in the present description.

In the present embodiment, the processor 230 in the electronic device 204 comprises a glucose level estimation module 238, a NADH feature point identification module 240, a NADH feature vector identification module 242, and a model selection module 244. Preferably, the processor 230 are arranged to receive, store, and execute appropriate computer instructions or codes so as to process and analyse data received from the measurement device 202. In the present embodiment, the processor 230 is arranged to process the data received from the measurement device 202 using machine learning algorithms (for example, SVM) that model the relationship between the NADH fluorescence decay and glucose concentration. The glucose estimation module 238 is arranged to process the data for glucose level estimation. The NADH fluorescence decay feature point identification module 240 is arranged to identify one or more feature points of NADH fluorescence decay based on the processed data. The NADH fluorescence decay feature vector identification module 242 is arranged to identify one or more feature vectors based on the one or more feature points identified. The model selection module 244 is arranged to select a glucose recession model to which the processed data should be applied to estimate the glucose concentration. In one embodiment, the model selection module 244 is arranged to select a glucose recession model specific to the user. The glucose estimation module 238 is arranged to apply the one or more feature vectors to the selected glucose regression model for estimation of the glucose concentration of the user.

The memory module 232 in the electronic device 204 is arranged to store the data received from the measurement device, the processed data, the selected glucose regression model, and/or the glucose estimation result. As described previously with respect to FIG. 2, the memory module 232 may be a volatile memory unit (such as RAM), a non-volatile unit (such as ROM, EPROM, EEPROM and flash memory), or both.

Input/output modules 236 may be provided in the electronic device 204. For example, the input/output modules 236 may include one or more control buttons, a microphone, a touch sensitive input device (e.g., screen), a display, a speaker, etc. In one embodiment, the electronic device 204 includes a touch control screen as the input/output modules 236. Preferably, a graphical user interface is provided by the input/output modules 236 so that the electronic device 204 can be controlled by a user and can display data, results, or other information to the user. The communication module 234 in the measurement device 202 enables data and/or power communication between the electronic device 204 and the measurement device 202 through a communication link C1, and data and/or power communication between the electronic device 204 and the database 206 through another communication link C2. Preferably, the communication module 234 is operable to transfer data and/or measurement results to the database for storage, and to retrieve suitable regression models from the database. In the present embodiment, the communication module 234 is a wireless communication module arranged to communicate with external devices through a wireless communication links C1, C2. The wireless communication link C2 may be a mobile broadband, Bluetooth, ZigBee, NFC, RFID, or Wi-Fi communication link. In some embodiments, the communication module 234 may be a wired communication module arranged to communication data and/or power with the measurement device 202 through a data and/or power cable. In some embodiments, the communication module 234 may be a wired communication module arranged to communication data and/or power with the database 206 through a data and/or power cable.

In the embodiment of FIG. 3, the database 206 includes a model database 260 arranged to store the modeled relationship between NADH fluorescence decay and glucose for glucose estimation. In one embodiment, the database 206 may be a server, for example a cloud server. The model database 260 may store one or more of: a personalized model based on personalized test data, a general model based on a collection of tests, or a combination of personalized and general models. Operation of the present invention using the personalized model requires individual data collection but fully reflects individual differences. On the other hand, operation using the general model does not need additional data collection from the individual but has lower accuracy. The combination of personal and general models, i.e., a hybrid model, is expected to achieve a better balance between individual preliminary test and accuracy. In a preferred embodiment, the database 206 can also be used to store the raw data obtained by measuring device 202 and the processed data and results obtained from electronic device 204 for other healthcare applications.

The operation of the system in FIGS. 2 and 3 in one embodiment of the present invention is illustrated below.

Step 1. Acquire NADH fluorescence decay using the measurement device 202 in the form of a lens-less, integrated time-correlated single photon counting (TCSPC) system.

The lens-less TCSPC system is applied to collect and analyze NADH fluorescence decay.

The light source (Nano LED-250 Pulsed LED 250 nm nominal, HORIBA) is arranged close to the skin of the user and is used to excite fluorescence reaction on NADH in dermal blood capillaries. The light source is preferably covered with fiber array to avoid light scattering, and with filter to ensure the wavelength in the UVA band, which is the NADH absorbance spectra.

The reflected or transmitted fluorescence light is collected by the SPAD (ID101, IDQ) sensor. The sensor is also covered with fiber array to avoid light scattering and with filter to ensure the wavelength is around 450 nm corresponding to the NADH emission spectra. Source light may be also further reduced by another UVA band pass filter if it is necessary to keep fluorescence photon rating around 1%.

The response time of every single fluorescence photon is measured in the TDC (TDC7200, TI) module by comparing time lapse between the arrival of fluorescence photon and the corresponding reference light Source pulse.

The peak measurement frequency depends on the frequency of light source. For Nano LED-250 Pulsed LED 250 nm nominal, the peak frequency is 1 MHz. Thus, at least over 10 k fluorescence photon arrival time data can be recorded within one second, By statistically analyzing the data through the data processing module, the NADH fluorescence decay can be computed in real-time.

Step 2. Identify the feature point of NADH fluorescence decay.

Statistical analysis and de-noising can be applied to the NADH fluorescence decay signal, which further include the following operations:

Photon arrival times are recorded and sorted statistically in a histogram form.

The signal processing methods (for example, low pass Butterworth filter for noise reduction) are applied to reduce noise influence.

Algorithm (for example, based on the Shannon power, illustrated below) is applied to identify peak of NADH fluorescence decay data.

The application of the Shannon algorithm is as follows:

First, each NADH fluorescence decay data is divided with the max value of among the data so that all the NADH fluorescence decay data is normalized within the region of [−1, 1].

Second, the Shannon power is calculated through equation (1).

$$E = -x^2 \log(x^2) \qquad (1)$$

where E is the Shannon power and x is the normalized NADH fluorescence decay data.

Third, the Shannon power is averaged through a moving time window expressed by:

$$E_A = \frac{1}{N} \sum_{i=1}^{N} E \qquad (2)$$

where E is the Shannon power, $E_A$ is the average Shannon and N is the length of the window.

Fourth, $E_A$ is normalized by subtracting the mean and dividing by the standard deviation, as expressed by:

$$E_N = \frac{E_A - M(E_A)}{S(E_A)} \qquad (3)$$

where $E_N$ is the normalized average Shannon energy, $M(E_A)$ and $S(E_A)$ are its mean value and standard deviation, respectively.

Fifth, a threshold is applied to $E_N$ to identify the potential peaks in NADH fluorescence decay.

Step 3. Generate feature vector of NADH fluorescence decay, which comprises:

Select a subset of NADH fluorescence decay data around the peak of the NADH fluorescence decay.

Normalize the intensity and length of the decay data subset.

Remove the baseline of the decay data subset. The baseline is defined as the line that passes through both the beginning and the end of the decay data subset.

In one embodiment, the proposed NADH fluorescence decay vectors identification module further includes:

A NADH fluorescence decay signal segmentation unit used to intercept the adjacent valley points or peak points.

A normalization unit used to normalize the segmented FLT signal.

A multi-dimensional FLT feature vector unit used to pick up designed number of feature point from normalized FLT signal to get multi-dimension FLT feature vector and the number of dimensions is the same as the designed number.

In some embodiments, step 3 further comprises

NADH fluorescence decay-glucose regression model is applied to estimate the blood glucose Signal processing method is applied to reduce noise influence Characteristic points of NADH fluorescence decay can be a series of feature values analyzed from the individual NADH fluorescence decay histogram unit including:

FLT value

Slope value of NADH fluorescence decay

NADH fluorescence decay itself

Central value of fitted NADH fluorescence decay with exponential function

Slope of NADH fluorescence decay and the NADH fluorescence decay can be directly obtained from the FLT histogram units. To get the FLT, the following step should be considered.

The instrument response function (IRF) needs to be recorded by the stray light of a diluted colloidal silica suspension for further calculation of an accurate FLT.

Using the histogram and IRF, FLT can be analyzed and fitted with the exponential model (4).

$$I(t) = \int_{-\infty}^{t} IRT(t') \sum_{i=1}^{n} A_i e^{\frac{t-t'}{\tau}} dt' \quad (4)$$

where A is the amplitude, t is the fluorescence lifetime, and 1 is the decay component.

The extend of the fit can be evaluated through statistical methods including correlation coefficient (CC), mean absolute error (MAE), mean error (ME) and standard deviation (SD) and the related equation have been shown as below:

$$CC = \frac{\sum_{i=1}^{n}(x_i - \bar{x})(y_i - \bar{y})}{\sqrt{\sum_{i=1}^{n}(x_i - \bar{x})^2}\sqrt{\sum_{i=1}^{n}(y_i - \bar{y})^2}} \quad (5)$$

$$MAE = \frac{1}{n}\sum_{i=1}^{n}|y_i - x_i| \quad (6)$$

$$ME = \frac{1}{n}\sum_{i=1}^{n}(y_i - x_i) \quad (7)$$

$$SD = \sqrt{\frac{1}{n-1}\sum_{i=1}^{n}(y_i - x_i - ME)^2} \quad (8)$$

Step 4. Model of the relationship between feature vector of FLT and glucose

The blood glucose and the NADH fluorescence decay are acquired synchronously.

A standard medical blood glucose meter can be applied to measure blood glucose. The glucose meter can be both invasive and non-invasive. During the test, insulin and sugar can be applied to cause fluctuation in blood glucose.

The acquired multi-dimensional NADH fluorescence decay feature vector is trained through SVM to get a glucose-NADH regression model.

The feature values of NADH fluorescence decay of each subject are further trained with corresponding results from a reference glucose test. SVM is used to build the regression model between NADH fluorescence decay and glucose level. For each subject, the SVM calculates the corresponding model between feature values of NADH fluorescence decay and glucose level. The method for identifying the relationship can also be other algorithms including Neural Network and Genetic Algorithm.

The machine learning based modeling can be checked through statistical methods including correlation coefficient (CC), mean absolute error (MAE), mean error (ME) and standard deviation (SD) as shown in equations (5)-(8).

Step 5. Apply the NADH fluorescence decay-glucose regression model for non-invasive estimation of blood glucose When the user wants to measure glucose level, he/she only needs to use the portable TCSPC to collect FLT signal of blood NADH on skin. The feature point of NADH fluorescence decay signal can be identified by the methods mentioned above. Then the corresponding NADH fluorescence decay-glucose regression model can be selected from a model base. By inputting the NADH fluorescence decay feature vector to the NADH fluorescence decay-glucose regression model, the glucose level can be estimated.

Figure 7:
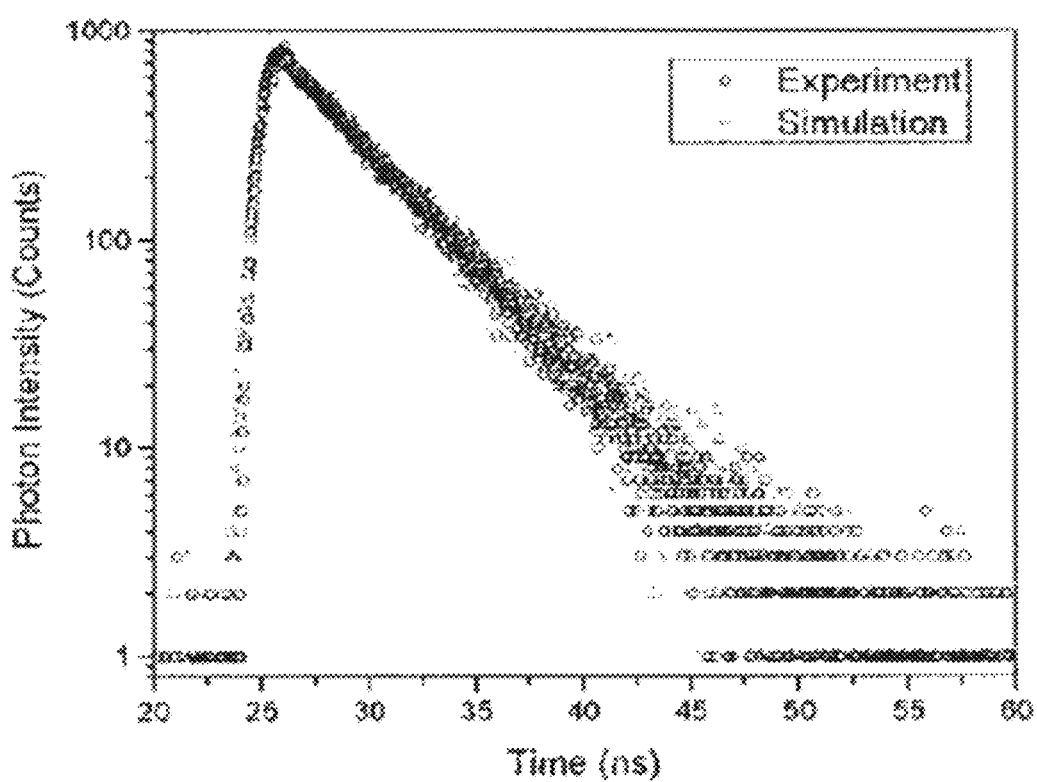
FIG. 7 is a graph showing experimental result showing a fluorescence decay measurement obtained using the method of FIG. 1 and using an alternative measurement method.

FIG. 7 is a graph showing experimental result showing a fluorescence decay measurement obtained using the method of FIG. 1 and using an alternative measurement method. In the experiment, a commercial TCSPC measurement equipment Deltapro is used. The excitation source is a Nano-LED with a 1.3 ns FWHM, 1 MHz repetition rate, and 7 pJ pulse energy. The fluorescent sample is the Rhodamine 6G in water.

The result in FIG. 7 indicates that the simulated decay fits well with the experiment decay. The fitting of the simulation and the experiment is also checked by the Pearson correlation coefficient (CC), mean absolute error (MAE), mean error (ME), standard deviation (SD), and Chi-square (CHISQ). The CC is 0.9953, which means that the simulation result and experiment result are strongly correlated. The MAE is 10, which means that for each time bin, the difference between the simulation and experiment is less than 10 photons. The ME is 0.5, which means that the simulation result is nearly unbiased to the experiment result. The SD is less than 8 photons, which means that the variations of the difference between the simulated result and measured result are small. The CHISQ is 2.12, which also shows good fitting of the simulation and experiment. These results suggest that this model can provide effective estimates of fluorescence lifetime TCSPC system with sufficient accuracy.

Figure 8:
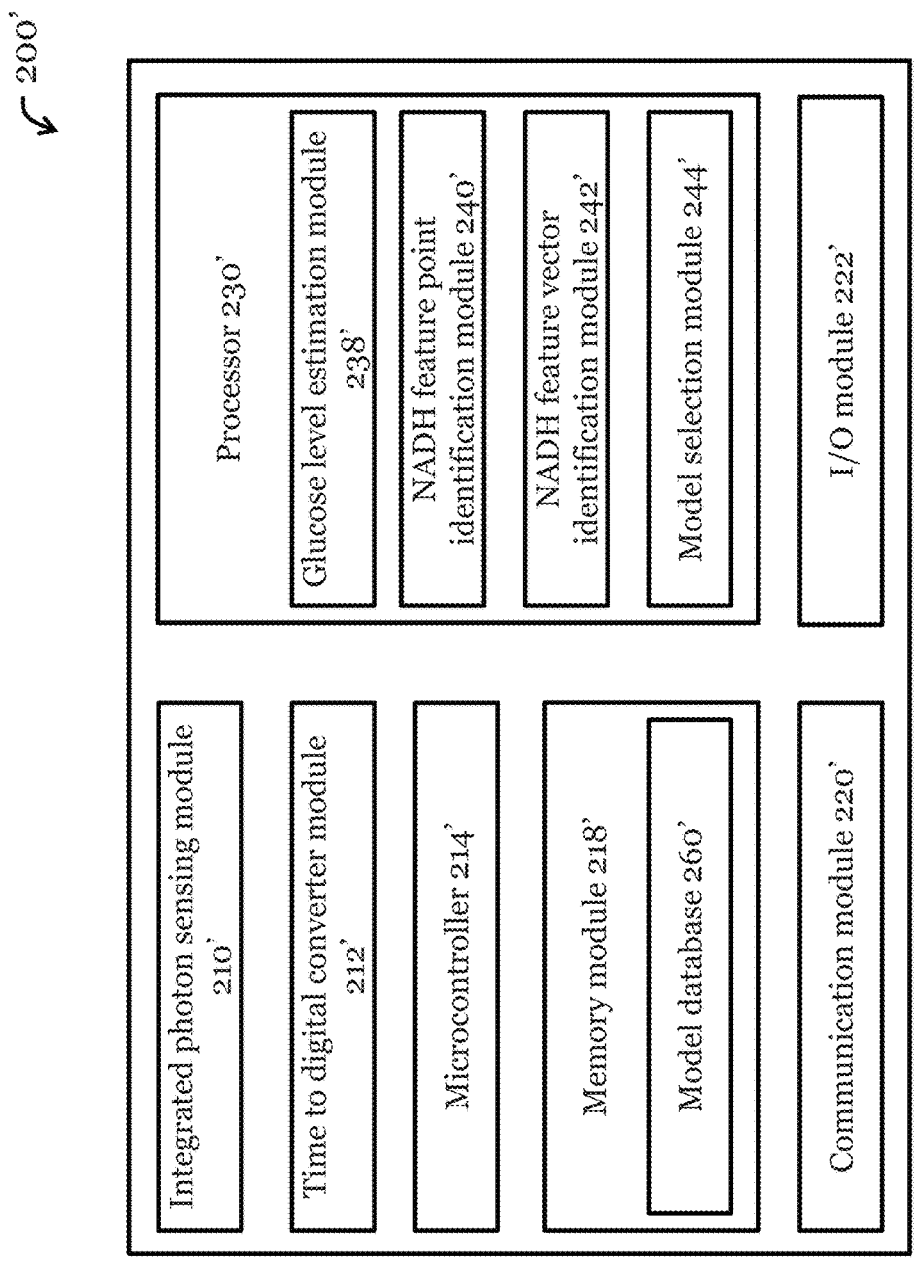
FIG. 8 is an illustration showing a system for implementing the method of FIG. 1 in accordance with another embodiment of the present invention.

FIG. 8 is a functional block diagram of another system 200' for implementing the method of FIG. 1 in accordance with one embodiment of the present invention. The function modules in the system 200' and those in system 200 of FIGS. 2 and 3 are substantially the same, and so like numbers are used to represent like modules. The main difference between the system 200' of FIG. 8 and the system 200 of FIG. 3 is that the system 200' incorporates all functional modules in a single device.

A person skilled in the art would appreciate that the methods and systems in the above embodiments of the present invention can be applied in different applications. In one example, the system may be used in hospitals and clinical environments. In particular, the proposed measurement device and system can be distributed to patients to allow the patients to perform self-monitoring at home, thereby reducing costly reliance at the hospital. Data analysis can be performed remotely at the hospitals or clinics. Also, results and data can be stored in a secure remote server. By using the method, system, and apparatuses of the above embodiments, patient data can be collected more timely and frequently. This in turn facilitates diagnostics and allows early detection of medical complications. In addition, quality of live can be improved through greater patient autonomy.

As the technique of the above embodiments of the present invention can be operated without the puncturing of skin and can be implemented using a wearable device. The embodiments of the present invention can operate in vivo, non-invasively, and continuously, and would cause minimal disturbance to the daily lives of users. Hence, it is suitable for long-term, real-time, and continuous glucose monitoring. Embodiments of the present invention enable a more rigorous blood glucose monitoring approach and hence can improve quality of life.

Further advantages of the technique proposed in the above embodiments of the present invention include:

Portable photon counting device is proposed for the wearable detection of NADH fluorescence decay. Feature points of NADH fluorescence decay are identified. Feature vector of NADH fluorescence decay is further generated based on feature point. The corresponding glucose regression model of the user is selected from the database of glucose regression. The user glucose levels are then estimated by importing the feature vector to the glucose regression model.

Unlike other non-invasive glucose monitoring technologies based on intensity detection, which are often influenced by photochemical processes like photo-bleaching, the fluorescence lifetime technology applied in this patent mainly depends on chemical structure of the target molecular instead of intensity. Therefore, it is more stable.

The photon counting module can work under high frequency (over 1 MHz). Thus, rapid and reliable result based on massive data statistics can be achieved.

The user only needs to collect a single type of bio-signal, the NADH fluorescence decay, through a wearable device. This process is non-invasive.

All in all, the above embodiments of the present invention provide an easy, low-cost, real-time, reliable and comfortable solution for daily monitoring of glucose level, which is especially useful for monitoring and prevention of adverse medical conditions.

It must again be stressed that the method, apparatus, and system described below are not limited in their application for glucose measurement, but can be used in other biological applications for measuring other analyte in different subject.

Although not required, the embodiments described with reference to the Figures can be implemented as an application programming interface (API) or as a series of libraries for use by a developer or can be included within another software application, such as a terminal or personal computer operating system or a portable computing device operating system. Generally, as program modules include routines, programs, objects, components and data files assisting in the performance of particular functions, the skilled person will understand that the functionality of the software application may be distributed across a number of routines, objects or components to achieve the same functionality desired herein.

It will also be appreciated that where the methods and systems of the present invention are either wholly implemented by computing system or partly implemented by computing systems then any appropriate computing system architecture may be utilized. This will include stand-alone computers, network computers and dedicated hardware devices. Where the terms "computing system" and "computing device" are used, these terms are intended to cover any appropriate arrangement of computer hardware capable of implementing the function described.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Any reference to prior art contained herein is not to be taken as an admission that the information is common general knowledge, unless otherwise indicated.

The invention claimed is:

1. A method for determining a concentration of an analyte in a subject, comprising the steps of:
   (a) irradiating a part of the subject with electromagnetic radiation, wherein the part of the subject comprising biological molecules arranged to absorb the electromagnetic radiation and to emit fluorescence in response;
   (b) measuring fluorescence emitted from the part of the subject to obtain data representative of a fluorescence decay;
   (c) processing the data to determine one or more feature points associated with the fluorescence decay and to generate one or more feature vectors based on the one or more feature points; and
   (d) applying the one or more feature vectors to a regression model for the analyte to determine the concentration of the analyte.

2. The method in accordance with claim 1, wherein step (a) comprises the step of:
   transmitting electromagnetic radiation in the form of pulses to the part of the subject.

3. The method in accordance with claim 2, wherein step (b) comprises the steps of:
   detecting fluorescence photons emitted from the part of the subject; and
   counting a number of fluorescence photons detected.

4. The method in accordance with claim 3, wherein step (b) further comprises the step of:
   determining, for each detected fluorescence photon, a response time based on a time difference between irradiation of electromagnetic radiation from which the respective fluorescence photon originates and detection of the respective fluorescence photon.

5. The method in accordance with claim 4, wherein the data represents a relationship between the number of fluorescence photons and the response time.

6. The method in accordance with claim 4, wherein the data represents a relationship between the number of fluorescence photons, a response time of fluorescence molecules from which the fluorescence photons are emitted, and chemical composition or process in which the fluorescence molecules reside.

7. The method in accordance with claim 1, wherein the step of processing the data to determine one or more feature points associated with the fluorescence decay comprises the steps of:
   filtering the data to reduce noise in the data; and
   applying a feature point identification method to the filtered data to identify one or more feature points from the data.

8. The method in accordance with claim 7, wherein the one or more features points comprise one or more peaks of the fluorescence decay, and the feature point identification method is a peak identification method.

9. The method in accordance with claim 8, wherein the peak identification method comprises the steps of:
- normalizing the data by dividing the data with a maximum value of the data;
- calculating a Shannon power using an equation $E=-x^2 \log(x^2)$, where E is the Shannon power and x is the normalized data;
- normalizing the averaged Shannon power; and
- applying a threshold to the normalized averaged Shannon power to identify the one or more peaks.

10. The method in accordance with claim 7, wherein the step of processing the data to generate one or more feature vectors based on the one or more feature points comprises the steps of:
- selecting a data subset from the filtered data based on the one or more feature points;
- processing the data subset; and
- generating the one or more feature vectors based on the processed data subset.

11. The method in accordance with claim 10, wherein the step of processing the data subset comprises the steps of:
- normalizing the data subset; and
- removing baseline of the data subset.

12. The method in accordance with claim 10, wherein the step of generating the one or more feature vectors based on the processed data subset comprises the step of:
- generating the one or more feature vectors using the processed data subset and one or more characteristics associated with the subject.

13. The method in accordance with claim 12, wherein the subject is a human or an animal, and the one or more characteristics associated with the subject comprises at least one of: age, weight, and body mass index of the subject.

14. The method in accordance with claim 8, wherein the step of generating one or more feature vectors based on the one or more feature points identified comprises the steps of:
- selecting a data subset around the one or more peaks of the fluorescence decay;
- normalizing an intensity and length of the data subset;
- removing a baseline of the data subset; and
- generating the one or more feature vectors based on the normalized data subset with baseline removed and one or more characteristics associated with the subject.

15. The method in accordance with claim 14, wherein the subject is a human or an animal, and the one or more characteristics associated with the subject comprises at least one of: age, weight, and body mass index of the subject.

16. The method in accordance with claim 1, wherein the one or more features points comprises one or more of:
- a fluorescence lifetime value associated with the fluorescence decay;
- a slope of the fluorescence decay; and
- a central value of the fluorescence decay fitted with an exponential function.

17. The method in accordance with claim 1, further comprising the step of:
- selecting the regression model from a plurality of regression models prior to step (d).

18. The method in accordance with claim 17, wherein the selected regression model is one of: a general regression model, a personalized regression model for the subject, and a hybrid regression model combining the general regression model and the personalized regression model.

19. The method in accordance with claim 1, further comprising the step of:
- creating the regression model.

20. The method in accordance with claim 19, wherein the step of creating the regression model comprises the steps of:
- (e) performing steps (a) to (c), and measuring the concentration of the analyte in a subject using another method at substantially the same time;
- (f) correlating one or more features vectors obtained from performing steps (a) to (c) and concentration of the analyte obtained from the another method so as to create the regression model.

21. The method in accordance with claim 20, further comprising the step of: repeating step (e); and
- training the regression model with one or more feature vectors using a machine learning based method.

22. The method in accordance with claim 21, wherein the machine learning based method utilizes a support vector machine model.

23. The method in accordance with claim 1, wherein the subject is a human or an animal, the biological molecules comprise a reduced form of nicotinamide adenine dinucleotide, the analyte comprises glucose, and the method is performed in vivo.

24. A system for determining a concentration of an analyte in a subject, comprising:
- a source of electromagnetic radiation arranged to irradiate a part of the subject, wherein the part of the subject comprising biological molecules arranged to absorb the electromagnetic radiation and to emit fluorescence in response;
- a measurement unit arranged to measure fluorescence emitted from the part of the subject to obtain data representative of a fluorescence decay; and
- a processor arranged to process the data to determine one or more feature points associated with the fluorescence decay and to generate one or more feature vectors based on the one or more feature points, and apply the one or more feature vectors to a regression model for the analyte to determine the concentration of the analyte.

25. The system in accordance with claim 24, wherein the source of electromagnetic radiation is arranged to transmit electromagnetic radiation in the form of pulses to the part of the subject.

26. The system in accordance with claim 25, wherein the measurement unit comprises a detector arranged to detect fluorescence photons emitted from the part of the subject and a counter arranged to count a number of fluorescence photons detected.

27. The system in accordance with claim 26, wherein the processor or a processing sub-unit in the measurement unit is arranged to determine, for each detected fluorescence photon, a response time based on a time difference between irradiation of an electromagnetic radiation from which the respective fluorescence photon originates and collection of the respective fluorescence photon.

28. The system in accordance with claim 27, wherein the data represents a relationship between the number of fluorescence photons and the response time.

29. The system in accordance with claim 24, wherein the processor is arranged to filter the data to reduce noise in the data, and to apply a feature point identification method to the filtered data to identify one or more feature points from the data.

30. The system in accordance with claim 29, wherein the processor is arranged to select a data subset from the filtered data based on the one or more feature points; process the data subset; and generate the one or more feature vectors based on the processed data subset.

31. The system in accordance with claim 30, wherein the processor is further arranged to generate the one or more feature vectors using the processed data subset and one or more characteristics associated with the subject.

32. The system in accordance with claim 31, wherein the subject is a human or an animal, and the one or more characteristics associated with the subject comprises at least one of: age, weight, and body mass index of the subject.

33. The system in accordance with claim 24, wherein the processor is further arranged to select the regression model from a plurality of regression models; wherein the selected regression model is one of: a general regression model, a personalized regression model for the subject, and a hybrid regression model combining the general regression model and the personalized regression model.

34. The system in accordance with claim 24, wherein the subject is a human or an animal, the biological molecules comprise a reduced form of nicotinamide adenine dinucleotide, and the analyte comprises glucose.

35. A measurement device for facilitating determination of a concentration of an analyte in a subject, comprising:
a light source arranged to irradiate a part of a subject, wherein the part of the subject comprising biological molecules arranged to absorb the electromagnetic radiation and to emit fluorescence in response;
a detector arranged to detect fluorescence emitted from the part of the subject so as to obtain data representative of a fluorescence decay;
a time to digital converter module operably connected with the detector, the time to digital converter module being arranged to determine, for each fluorescence photon, a response time based on a time difference between irradiation of the light from which the respective fluorescence photon originates and collection of the respective fluorescence photon;
a processor operably connected with the detector and the time to digital converter module to process data obtained by the detector and the time to digital converter module, the data representing a relationship between the number of fluorescence photons and the response time; and
a communication module operably connected with the processor, the communication module being arranged to transfer the data to a remote information handling system for processing and analysis,
wherein the remote information handling system includes:
a communication module arranged to receive the data transferred from the communication module of the measurement device; and
a processor arranged to process the data to determine one or more feature points associated with the fluorescence decay and to generate one or more feature vectors based on the one or more feature points, and apply the one or more feature vectors to a regression model for the analyte to determine the concentration of the analyte.

36. The measurement device of claim 35, wherein the light source is a high frequency light source comprising an LED or a laser emitter.

37. The measurement device of claim 35, wherein the light source is arranged to provide pulsed light.

38. The measurement device of claim 35, wherein light emitted by the light source comprises a wavelength of 310 nm to 400 nm.

39. The measurement device of claim 35, wherein the detector is a single photon avalanche diode or a photomultiplier tube arranged to count a number of fluorescence photons.

40. The measurement device of claim 35, further comprising at least one of an excitation filter and an emission filter, the excitation filter is arranged to filter light emitted from the light source such that the filtered light is adapted for absorption by the biological molecules; and the emission filter is arranged to filter light emitted from the light source such that the filtered light is adapted for absorption by the biological molecules.

41. The measurement device of claim 40, further comprising a fibre-optic array or a collimator arranged to concentrate the filtered light.

42. The measurement device of claim 35, further comprising at least one of an excitation filter and an emission filter, the excitation filter is arranged to filter fluorescence emitted from the part of the subject such that the filtered light is adapted for detection by the detector; and the emission filter is arranged to filter fluorescence emitted from the part of the subject such that the filtered light is adapted for detection by the detector.

43. The measurement device of claim 42, further comprising a fibre-optic array or a collimator arranged to concentrate the filtered light.

44. The measurement device of claim 35, wherein the light source and the detector are arranged on the same side with respect to the part of the subject.

45. The measurement device of claim 35, wherein the light source and the detector are arranged on opposite sides with respect to the part of the subject.

46. The measurement device of claim 35, wherein the communication module of the measurement device is a wireless communication module.

47. The measurement device of claim 35, wherein the measurement device is portable.

48. The measurement device of claim 35, wherein the remote information handling system is a portable electronic device.

49. The measurement device of claim 35, wherein the communication module of the remote information handling system is further arranged to:
transfer the data to a database for storage; and
obtaining one or more regression models from a database with a plurality of regression models for the analyte.

50. The measurement device of claim 49, wherein the processor of the remote information handling system is further arranged to select a regression model from the regression models obtained.

51. The measurement device of claim 49, wherein the database is formed by a server.

52. The measurement device of claim 35, wherein the subject is a human or an animal, the biological molecules comprise a reduced form of nicotinamide adenine dinucleotide, and the analyte comprises glucose.

* * * * *